United States Patent [19]
Bourgeois

[11] Patent Number: 5,995,872
[45] Date of Patent: *Nov. 30, 1999

[54] METHOD AND APPARATUS FOR ELECTRICAL STIMULATION OF THE GASTROINTESTINAL TRACT

[75] Inventor: Ivan Bourgeois, Verviers, Belgium

[73] Assignee: Medtronic, Inc., Minneapolis, Minn.

[ * ] Notice: This patent is subject to a terminal disclaimer.

[21] Appl. No.: 09/164,264

[22] Filed: Oct. 1, 1998

Related U.S. Application Data

[63] Continuation of application No. 08/846,786, Apr. 30, 1997, Pat. No. 5,836,994.

[51] Int. Cl.$^6$ .................................................. A61N 1/36
[52] U.S. Cl. ............................... 607/40; 607/72; 607/33
[58] Field of Search .................................. 607/40, 41, 72, 607/73, 133, 138, 143; 600/29, 30

[56] References Cited

U.S. PATENT DOCUMENTS

| | | |
|---|---|---|
| 4,981,470 | 1/1991 | Bombeck, IV . |
| 5,188,104 | 2/1993 | Wernicke et al. . |
| 5,292,344 | 3/1994 | Douglas . |
| 5,836,994 | 11/1998 | Bourgeois ................................. 607/40 |

FOREIGN PATENT DOCUMENTS

| | | |
|---|---|---|
| 2 237 648 | 7/1973 | France . |
| 2 453 630 | 4/1979 | France . |
| 0571 938 A2 | 5/1993 | Germany . |
| 1651918A1 | of 0000 | U.S.S.R. . |
| WO 94/27672 | 5/1994 | United Kingdom . |

OTHER PUBLICATIONS

Ergebnisse der Inneren Medizin und Kinderheilkunde—16:198 (1961) (cover page).
Electric Stimulation of the Gastrointestinal Tract—GP Apr. 1994.

Primary Examiner—Jeffrey R. Jastrzab
Attorney, Agent, or Firm—Thomas F. Woods; Harold Patton; Michael J. Jaro

[57] ABSTRACT

A method and apparatus for providing electrical stimulation of the gastrointestinal tract. The apparatus features an implantable pulse generator which may be coupled to the gastric system through one or more medical electrical leads. In the preferred embodiment the leads couple to the circular layer of the stomach. The pulse generator preferably features sensors for sensing gastric electrical activity, and in particular, whether peristaltic contractions as occurring. In particular two sensors are featured. The first sensor senses low frequency gastrointestinal electrical activity between the frequency of 0.017–0.25 Hz and the second sensor senses intrinsic gastrointestinal electrical activity between the frequency of 100–300 Hz, which occurs upon normal peristaltic contractions. The second sensor only senses for a preset period after low frequency gastrointestinal electrical activity has been sensed by the first sensor. The pulse generator further delivers stimulation pulse trains to the gastrointestinal tract at a period of time after low frequency gastrointestinal electrical activity has been sensed by the first sensor. If, however, the second sensor senses intrinsic gastrointestinal electrical activity between the frequency of 100–300 Hz, then the delivery of stimulation pulse trains to the gastrointestinal tract is inhibited. In such a manner the present invention detects the occurrence of normal peristaltic contractions and further provides electrical stimulation to the gastrointestinal tract if such normal peristaltic contrations are not detected.

19 Claims, 11 Drawing Sheets

OTHER PUBLICATIONS

Gastrointestinal Pacing—A New Concept in the Treatment of Ileus—Biomedical Sciences Instrumentation vol. 1. 1963 (A.M. Bilgutay, R. Wingrove, W.O. Griffen, R.C. Bonnabeau and C.W. Lillehei).

Gastro–intestinal Pacing: Will It Work?—American Journal of Surgery, Feb. 1966 (J. Sonneland).

Evaluation of the Intrinsic Innervation of the Internal Anal Sphincter using Electrical Stimulation—Gut, 1989, 30, 935–938 (M.A. Kamm, J.E. Lennard–Jones, and R.J. Nicholls).

Enhancing Absorption in the Canine Short Bowel Syndrome by Intestinal Pacing—Surgery, Aug. 1980 (H.E. Gladen and K.A. Kelly).

Pacing the Human Stomach—Surgery, Feb. 1992 (B.W. Miedema, M.G. Sarr and K.A. Kelly).

Ectopic Jejunal Pacemakers and Gastric Emptying after Roux Gastrectomy: Effect of Intestinal Pacing—Surgery, Nov. 1989 (L. Karlstrom and K.A. Kelly).

A New Treatment for Rectal Prolapse (Abridged)—Proceedings of the Royal Society of Medicine (K.P.S. Caldwell).

Prognosis of Patients with an Ileostomy—Section of Proctology (A.G. Parks).

(List continued on next page.)

Differential Responses of the Canine Gastric Corpus and Antrum to Electric Stimulation—American Journal of Physiology, Jan. 1974 (K.A. Kelly).

The Electrical Control of Sphincter Incompetence—The Lancet, Jul. 23, 1963 (K.P.S. Caldwell).

Gastric Motor Physiology and Pathophysiology—Surgical Clinics of North America, vol. 73, Dec. 1993 (J.J. Cullen and K.A. Kelly).

The Role of the Extrinsic Antral Nerves in the Regulation of Gastric Emptying—Surgery, Gynecology & Obstetrics, Sep. 1977, vol. 145 (C.T. Mroz and K.A. Kelly).

A New Treatment for Rectal Prolapse—Geriatrics, Jan. 1968 (K.P.S. Caldwell).

Incontinence—Transactions of The Medical Society of London, Ordinary Meeting, Apr., 1973 (K.P.S. Caldwell).

The Treatment of Incontinence—Hospital Management (K.P.S. Caldwell).

Control of Gastro–intestinal Motility with Electrical Pacing—Jap. J. Smooth Muscle Res. 21: Suppl., 125, 1985 (H.M. Richter, III, S. Bjorck and K.A. Kelly).

Effect of Electrical Stimulation on Gastric Electrical Activity, Motility and Emptying—Neurogastroenterology and Motility 1995 (J.C. Eagon and K.A. Kelly).

Independence of Canine Gastric and Duodenal Pacesetter Potentials Shown by Electric Pacing—May Clin. Proc, Jan. 1977, vol. 52 (H.E. Gladen and K.A. Kelly).

Duodenal–Gastric Refulx and Slowed Gastric Empyting by Electrical Pacing of the Canine Duodenal Pacesetter Potential—Gastroenterology 72:429–433, Mar. 1977 (K.A. Kelly and C.F. Code).

Pacing the Human Gut—The American Journal of Gastroenterology, vol. 89, No. 3, 1994 (D.A. Johnson and E.L. Cattau).

Pacing the Gut—Gastroenterology, Dec. 1992 (K.A. Kelly).

Human Gastric Myoelectric Activity and Gastric Emptying Following Gastric Surgery and With Pacing—1992 Gastroenterological (M.P. Hocking, S.B. Vogel and C.A. Sninsky).

Pacing the Canine Stomach with Electric Stimulation—American Journal of Physiology, Mar. 1972 (K.A. Kelly and R.C. La Force).

Gastric Emptying of Liquids and Solids: Roles of Proximal and Distal Stomach—Editorial Review, The American Physiological Society 1980 (K.A. Kelly).

Electric Pacing of Intact and Transected Canine Small Intestine and its Computer Model—American Journal of Physiology, vol. 229, Nov. 1975 (O.E. Akwari, K.A. Kelly, J.H. Steinbach and C.F. Code).

Electrical Treatment of Anal Incontinence—The Lancet, Feb. 5, 1966 (B.R. Hopkinson, R. Lightwood).

Electrophysiology of Human Colon Motility in Health and Disease—Clinics in Gastroenterology, vol. 15, No. 4, Oct. 1986 (J.D. Huizinga).

Cerebral Evoked Potentials After Rectal Stimulation—Electroencephalography and Clinical Neurophysiology, 80 (1991) 490–495 (V. Loening–Baucke, N.W. Read and T. Yamada).

Measurement of Gastric and Small Bowell Electrical Activity at Laparoscopy—Journal of Laparoendoscopic Surgery, vol.4, No. 5, 1994 (B.O. Familoni, T.L. Abell and G. Voeller).

Electrical Stimulation of the Bowel—Arch Surg. vol. 91, Sep. 1965 (J.M. Moran and D.C. Nabseth).

Electrical Pacing for Short Bowel Syndrome—Surgery, Gynecology & Obstetrics—Nov. 1981, vol. 153 (H.E. Gladen and K.A. Kelly).

The Treatment of Incontinence by Electronic Implants—Annals of The Royal College of Surgeons of England, Dec. 1967 (K.P.S. Caldwell).

The Future of Intestinal Pacing—Gastroenterology Clinics of North America, vol. 23, No. 2, Jun. 1994 (J.J. Cullen and K.A. Kelly).

Control of Muscle Tone in the Human Colon—Gut, 1992, 33, 541–546 (C.J. Steadman, S.F. Phillips, M. Camilleri, N.J. Talley, A. Haddad, R. Hanson).

Enhancing the Anti–Dumping Effect of Roux Gastrojejunostomy with Intestinal Pacing—Ann. Surgery, Oct. 1983, vol. 198 (B. Cranley, K.A. Kelly, V.L.W. Go, L.A. McNichols).

The Roux Operation for Postgastrectomy Syndromes—The American Journal of Surgery, vol. 161, Feb. 1991 (B.W. Miedema, K.A. Kelly).

Effect of Duodenal Cooling on Small Intestinal Pacing—Mayo Clin. Proc. Aug. 1982, vol. 57 (K.R. Berg, H.E. Gladen, K.A. Kelly).

Achieving Enteric Continence: Principles and Applications—Mayo Clin Proc. Jul. 1986, vol. 61 (J.H. Pemberton, K.A. Kelly).

Electrical Stimulation of the Human Stomach—Digestive Diseases and Sciences, vol. 30, No. 8, Aug. 1985 (W.E. Waterfall, D. Miller, D.N. Ghista).

Gastric Electrical Stimulation as a Possible New Therapy for Patients with Severe Gastric Stasis—Gastroenterology, vol. 100, No. 5, Part 2 (T.L. Courtney, B.D. Schirmer, B.E. Ballahsene, O.L. Updike and R.W. McCallum).

Temporary and Permanent Electrical Stimulation of the Human Stomach Using High Frequency Pacing—Motility and Nerve–Gut Interactions, Apr. 1993 (B.O. Familoni, T.L. Abell, G. Voeller, A. Salem, O. Gaber, D. Nemoto).

Long–Term Electrical Stimulation of the Human Stomach—Gastroenterology, vol.106, No. 4, Part 2 (B.O. Familioni, T.L. Abell, G. Voeller, A. Salem, O. Gaber, D. Nemoto).

A Model of Gastric Electrical Activity in Health and Disease—IEEE Transactions on Biomedical Engineering, vol. 42, No. 7, Jul. 1995 (B.O. Familoni, T.L. Abell, K.L. Bowes).

Use of Spectral Analysis in the Detection of Frequency Differences in the Electrogastrograms of Normal and Diabetic Subjects—IEEE Transactions on Biomedical Engineering, vol. 35, No. 11, Nov. 1988 (C.J. Pfister, J.W. Hamilton, N. Nagel, P. Bass, J.G. Webster and W.J. Tompkins).

Gastric Motility after Gastric Operations—Surgery Annual 1974 (K.A. Kelly).

Electrical Stimulation of Gastric Electrical Control Activity—American Journal of Physiology, vol. 225, No. 1, Jul. 1973 (S.K. Sarna and E.E. Daniel).

Electrical Pacing of the Roux Limb Resolves Delayed Gastric Emptying—Journal of Surgical Research 42, 635–641 (1987) (A. Sawchuk, D. Canal, J.L. Grosfeld, <. Slaughter, G. Gardner, T. O'Connor and D. Behrman).

Gastrointestinal Pacing—Staff Report Meeting—Univeristy of Minnesota Medical Bulletin 1965 (A.M. Bilgutay, R. Wingrove, W.O. Griffen, A. Nakib, R.C. Bonnabeau, C.W. Lillehei).

Acceleration of Gastric Emptying with Electrical Stimulation in a Canine Model of Gastroparesis—1992 the American Physiology Society (B–E Bellahsène, C.D. Lind, B.S. Schirmer, O.L. Updike and R.W. McCallum).

A Trial of a Gastro–intestinal Pacemaker—Journal of the Irish Medical Association Jan. 1966 (P.N. Fitzpatrick, and A.W. Chen).

Behavioral and Gastrointestinal Changes (Motility and Blood Flow) Induced by Electrical Stimulation of the Lateral Hypothalamus in Cats—Abstr. XI Scand. Physiol. Congr. Copenmhagen 1963, Suppl. No. 213 (F. Björn and E.H. Rubinstein).

Gastrointestinal Pacemaker—The Lancet, Dec. 7, 1963 (J.M. Sanchez).

Gastrointestinal Pacing—Modern Medicine, Mar. 15, 1965 (A.M. Bilgutay, R. Wingrove, W.O. Griffen, A. Nakib, R.C. Bonnabeau and C.W. Lillehei).

Response to Gastrointestinal Pacing: Antral, Duodenal and Jejunal Motility in Control and Postoperative Patients—Annals of Surgery, Jul. 1966 (T. Berger, J. Kewenter, N.G. Kock).

Evaluation of a Portable Gastric Stimulator—IEEE/9th Annual Conference of the Engineering in Medicine and Biology Society, 1987 (B–E. Bellahsene, R. W. McCallum, O.T. Updike).

Role of Gastric Pacesetter Potential Defined by Electrical Pacing—Canadian Journal of Physiology and Pharmacology, vol. 50, Oct. 1972 (K.A. Kelly and R.C. La Force).

The Endomotorsonde—A New Device for Studying the Gastrointestinal Tract—The American Journal of Medical Electronics, Jul.–Sep. 1964 (J.P.M. D'Haens).

Electronic Pacemakers of the Heart, Gastrointestinal Tract, Phrenic Nerve, Bladder and Carotid Sinus: Current Status—Surgery, Aug. 1966, vol. 60, No. 2 (C.E. Anagnostopoulos, W.W.L. Glenn).

Control of Postoperative Adynamic Bowel in Dogs by Electric Stimulation—vol. IX Trans. Amer. Soc. Artif. Int. Organs, 1963 (D. R. de Villiers, I. Saltiel, A. Nonoyama and A. Kantrowitz).

Reverse Electrical Pacing Improves Intestinal Absorption and Transit Time—Surgery, vol. 100, No.2, Aug. 1986 (A. Sawchuk, W. Nogami, S. Goto, J. Yount, J.A. Grosfeld, J. Lohmuller, M.D. Grosfeld and J.L. Grosfeld).

External Stimulation of Gastric Antrum and Gastric Secretion—The American Journal of Gastroenterology, vol. 52, No. 6, Dec. 1969 (P. Lott, T. Geisel, N.C. Jefferson and H. Necheles).

Electrical Activity of the Gastric Antrum in Normal Human Subjects—The American Journal of Digestive Diseases, vol. 16, No. 7, Jul. 1971 (H. Monges and J. Salducci).

Gastric Pacemakers—Gastroenterology, vol. 70, No. 2, Feb. 1976 (S.K. Sarna, K.L. Bowes and E.E. Daniel).

Apparatus for Electrical Stimulation of Weakened Peristaltic Activity of the Stomach Experimental Investigation)—Biomedical Eng. Mar.–Apr. 1973 (M.A. Sobakin and V.A. Shepelev).

Clinical Evaluation of the Gastrointestinal Pacer—Surgery, Gynecology & Obstetrics, Jan. 1965 (D.C. Quast, A.C. Beall and M.E. DeBakey).

Electrostimulation of the Small and the Large Bowel in Dogs—Biomedical Sciences Instrumentation, May, 1969 (G. Járos and C.R. Jansen).

Clinical Experience in Control of Postoperative Adynamic Ileus by Electric Stimulation—Surgical Forum, Vo.. 14, 1963 (D.R. de Villiers, I. Saltiel, A. Nonoyama and A. Kantrowitz).

Electric Treatment of Intestinal Obstruction and Postoperative Paralysis of the Bowel—Jour. A.M.A., Apr. 1, 1911 (W.H. Dieffenbach).

Studies in Electrical Stimulation of the Adynamic Bowel—The American Journal of Gastroenterology, vol. 44, 1965 (A. Kantrowitz).

Electrical Activity of the Gastrointestinal Tract as an Indication of Mechanical Activity—American Journal of Digestive Diseases, vol. 8, 1963 (E.E. Daniel and K.M. Chapman).

Relative Electrical Impedance as Index of Intestinal Viability—Archives of Surgery, vol. 89, Jul. 1964 (L.C. Carey, K. Keyser, E.H. Ellison and D. Lepley).

Controlled Radiological Evaluation of an Intestinal Pacemaker (Peristart)—Scand. J. Gastroent., 1966, vol. 1 (P. Bach–Nielsen, H. Baden and A.M. Christensen).

An Improved Method for Recording and Analyzing the Electrical Activity of the Human Stomach—IEEE Transactions on Biomedical Engineering, vol. 32, No. 11, Nov. 1985 (B.E. Bellahsene, J.W. Hamilton, J.G. Webster, P. Bass and M. Reichelderfer).

Study of Transcutaneous and Intraluminal Measurement of Gastric Electrical Activity in Humans—Medical & Biological Engineering & Computing, Jul. 1987 (B.O. Familoni, Y.J. Kingma and K.L. Bowes).

Human Gastric Myoelectric Activity and Gastric Emptying Following Gastric Surgery and With Pacing—Gastroenterology, 1992, vol. 103, No. 6 (M.P. Hocking, S. B. Vogel and C.A. Sninsky).

Programmer Medtronic 7432 and Memory Mod 7455—Clinical Plan Gastroparesis, Mar. 2, 1994.

Electrical Pacing of the Stomach in Dogs—IEEE, Sep. 1992 (B.O. Familoni, T.L. Abell).

Gastroparesis and the Current Use of Prokinetic Drugs—The Gastroenterologist, vol. 1 No. 2, Jun. 1993 (B.J. Kendall and R.W. McCallum).

Physiology of the Colon and Rectum—The American Journal of Surgery, vol. 117, Jun. 1969 (R.D. Williams and J.W. Dickey).

Effects of Gastric Pacing on Canine Gastric Motility and Emptying—American Journal of Physiology, vol. 265, No. 4, Oct. 1993 (J.C. Eagon and K.A. Kelly).

Manometric Evaluation of Children with Chronic Constipation Using a Suction Stimulating Electrode—Eur. J. Pediatr. Surg. 2 (1992)287–290 (M. Kubota, A. Nagasaki and K. Sumitomo).

"High Prevalence of Gastric Electrical Dysrhythmias InDiabetic Gastroparesis"—T.L. Abell et al. (Gastroenterology, 1985; 88:1299).

"Development of a Canine Model for Gastric Pacing"—B. Johnson et al. (Gastroenterology, vol. 98, No. 5, Part 2).

"Postoperative Gastroparesis and Tachygastria—Response to Electric Stimulation and Erythromycin"—M.P. Hocking (Surgery, vol. 114, No. 3, Sep. 1993, pp. 538–542).

"Electrogastrographic Study of Gastric Myoelectrical Activity in Patients with Unexplained Nausea and Vomiting"—H. Geldof et al. (Gut, 1986, vol. 27, pp. 799–808).

"Efficacy of Electrical Stimulation at Frequencies Higher than Basal Rate in Canine Stomach"—B. Familioni et al. (Digestive Diseases and Sciences, vol. 42 No. 5, May 1997, pp. 892–897).

"Analysis of Gastric Emptying Data"—J.D. Elashoff et al (Gastroenterology 1982: 83:pp. 1306–1312).

"Gastric Myoelectric Activity in Patients with Chronic Idiopathic Gastroparesis"—M. Bortolotti et al. (Gastrointestinal Motility, vol. 2, No. 2, Jun. 1990, pp. 104–108).

GastricElectromechanical and Neurohormonal Function in Anorexia Nervosa:—T.L. Abell et al. (Gastgroenterology, Nov. 1987:93: pp. 958–965).

Electrogastrography—Current Assessment and Future Perspectives—T.L. Abell et al. (Digestive Diseases and Sciences, vol. 33, No. 8, Aug. 1988, pp. 982–992).

Electrogastrographic Study of Patients with Unexplained Nausea, Bloating and Vomiting—C.H. You et al. (Gastroenterology, vol. 79, No. 2, Aug. 1980, pp. 311 314).

"Motility of the Stomach and Gastroduodenal Junction"—K.A. Kelly (Physiology of the Gastrointestinal Tract, 1981, pp. 393–410).

"Gastric Dysrhythmias and Nausea of Pregnancy"—K.L. Koch et al. (Digestive Diseases and Science, vol. 35, No. 8, Aug. 1990, pp. 961–968).

METHOD AND APPARATUS FOR ELECTRICAL STIMULATION OF THE GASTROINTESTINAL TRACT

This application is a continuation of application Ser. No. 08/846,786, filed Apr. 30, 1997, now U.S. Pat. No. 5,836,994.

FIELD OF THE INVENTION

The invention relates to treatment of gastrointestinal disorders using a method and apparatus for providing electrical stimulation of the gastrointestinal tract.

BACKGROUND OF THE INVENTION

The gastrointestinal tract is responsible for an essential step in the digestive process, the reception of nutrition in the human body. An important element of the digestive process is peristalsis, the coordinated and self-regulated motor activity of the intestinal tract. Peristalsis is accomplished through a coordinated combination of electrical, chemical, neurological and hormonal mediation, as well as possibly other, as yet unknown, mechanisms.

Many diseases and maladies can affect the motor activity of the gastrointestinal tract, causing malfunction of the digestive process. Such diseases include diabetes mellitus, scieroderma, intestinal pseudo-obstruction, ileus, and gastroparesis.

Gastroparesis, for example, is a chronic gastric motility disorder in which there is delayed gastric emptying of solids and/or liquids. Symptoms of gastroparesis may range from early satiety and nausea in mild cases to chronic vomiting, dehydration, and nutritional compromise in severe cases. Diagnosis of gastroparesis is based on demonstration of delayed gastric emptying of a radio-labeled solid meal in the absence of mechanical obstruction. Gastroparesis may occur for a number of reasons. Approximately one third of patients with gastroparesis, however, have no identifiable underlying cause (often called idiopathic gastroparesis). Management of gastroparesis involves four areas: (1) prokinetic drugs, (2) antiemetic drugs, (3) nutritional support, and (4) surgical therapy (in a very small subset of patients.) Gastroparesis is often a chronic, relapsing condition; 80% of patients require maintenance antiemetic and prokinetic therapy and 20% require long-term nutritional supplementation. Other maladies such as tachygastria or bradygastria can also hinder coordinated muscular motor activity of the gastrointestinal tract, possibly resulting in either stasis or nausea or vomiting or a combination thereof.

The undesired effect of these conditions is a reduced ability or complete failure to efficiently propel intestinal contents down the digestive tract. This results in malassimilation of liquid or food by the absorbing mucosa of the intestinal tract. If this condition is not corrected, malnutrition or even starvation may occur. Moreover nausea or vomiting or both may also occur. Whereas some of these disease states can be corrected by medication or by simple surgery, in most cases treatment with drugs is not adequately effective, and surgery often has intolerable physiologic effects on the body.

Presently, however, there is no practically effective device or system to stimulator intelligently alter the muscular contractions of smooth muscle and the gastrointestinal tract in particular. Therefore, there is a need in the art for a system and method to properly stimulate the gastrointestinal tract to thereby treat ineffective or absent electrical muscular activity of the gastrointestinal tract.

SUMMARY OF THE INVENTION

It is an object of the invention to provide a method and apparatus for treating patients having dysfunctional gastrointestinal muscle or disorders of smooth muscles elsewhere in the body.

This and other objects are provided by one or more of the embodiments described below. The present invention is a method and apparatus for providing electrical stimulation of the gastrointestinal tract. The apparatus features an implantable pulse generator which may be coupled to the gastric system through one or more medical electrical leads. In the preferred embodiment the leads couple to the circular layer of the stomach. The pulse generator preferably features sensors for sensing gastric electrical activity, and in particular, whether peristaltic contractions as occurring. In particular two sensors are featured. The first sensor senses low frequency gastrointestinal electrical activity between the frequency of approximately 0.005 Hz–5 Hz ("slow waves") and the second sensor senses intrinsic gastrointestinal electrical activity between the frequency of approximately 100–5000 Hz ("spike activity") which occurs upon normal peristaltic contractions and immediately follows a slow wave. The second sensor only senses for a preset period after a slow waves has been sensed by the first sensor. The pulse generator further delivers stimulation pulse trains to the gastrointestinal tract at a period of time after slow waves have been sensed by the first sensor. If, however, the second sensor senses a sufficient amount of spike activity, then the delivery of stimulation pulse trains to the gastrointestinal tract is inhibited. In such a manner the present invention detects the occurrence of normal peristaltic contractions and further provides electrical stimulation to the gastrointestinal tract if such normal peristaltic contractions are not detected.

BRIEF DESCRIPTION OF THE DRAWINGS

The above-described and other aspects of the present invention may be better understood and appreciated with reference to a detailed description of a specific embodiment of the invention, when read in conjunction with the accompanying drawings, wherein.

The Figures are not necessarily to scale.

DETAILED DESCRIPTION OF THE INVENTION

Figure 1:
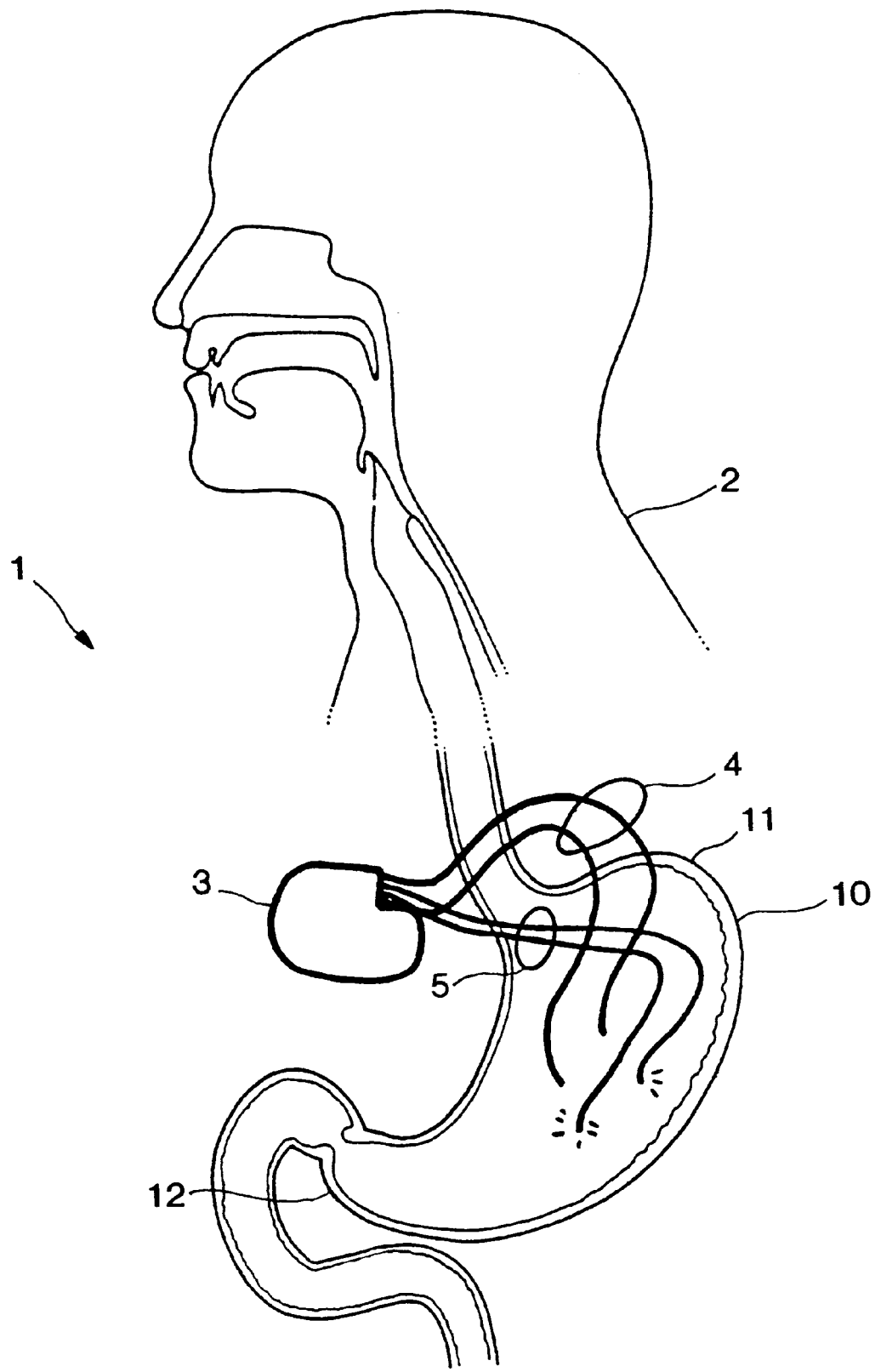
FIG. 1 depicts the apparatus implanted within a patient.

FIG. 1 shows a system 1 implanted in a patient 2. As seen, the system 1 comprises an implantable pulse generator 3 featuring two sets of leads 4, 5 which are coupled to the stomach 10. The first set of leads 4 provide stimulation to the stomach. The second set of leads 5 provide sensing of the gastroelectrical activity of the stomach 10 to the pulse generator 3. In the preferred embodiment, the pulse generator 3 is implanted within the patient 2. As such, the implantable pulse generator 3 features a hermetic enclosure, as is well known in the art. The leads used for both the first set 4 and the second set 5 may be any acceptable lead. In the preferred embodiment, the preferred leads are Medtronic Model No. 4300 intramuscular lead. Of course, other configurations of leads or lead systems may be used, including the use of from only a single lead, a single set of leads (i.e. two), or even the use of three or more sets of leads. Moreover, although shown as being coupled to the stomach it must be understood the present invention may be used along or on any of the other structures and organs along the gastrointestinal tract, including the colon, small intestine, stomach or even the esophagus.

The first set of leads 4 are stimulation leads which conduct stimulation pulses from the pulse generator 3 to the stomach 10. First set of leads 4 are preferably implanted through the serosa at the area within the transition of the corpus and the antrum on the great curvature. Of course, other locations for first set of leads 4 may be used, such as in the fundus, caudud corpus as well as the orad or terminal antrum. The second set of leads 5 are sensing leads which conduct any gastroelectrical activities sensed in the stomach 10 to the pulse generator 3. Preferably the second set of leads 5 are positioned distally in the mid antrum also along the great curvature, although these leads may also be positioned in other locations.

Figure 2:
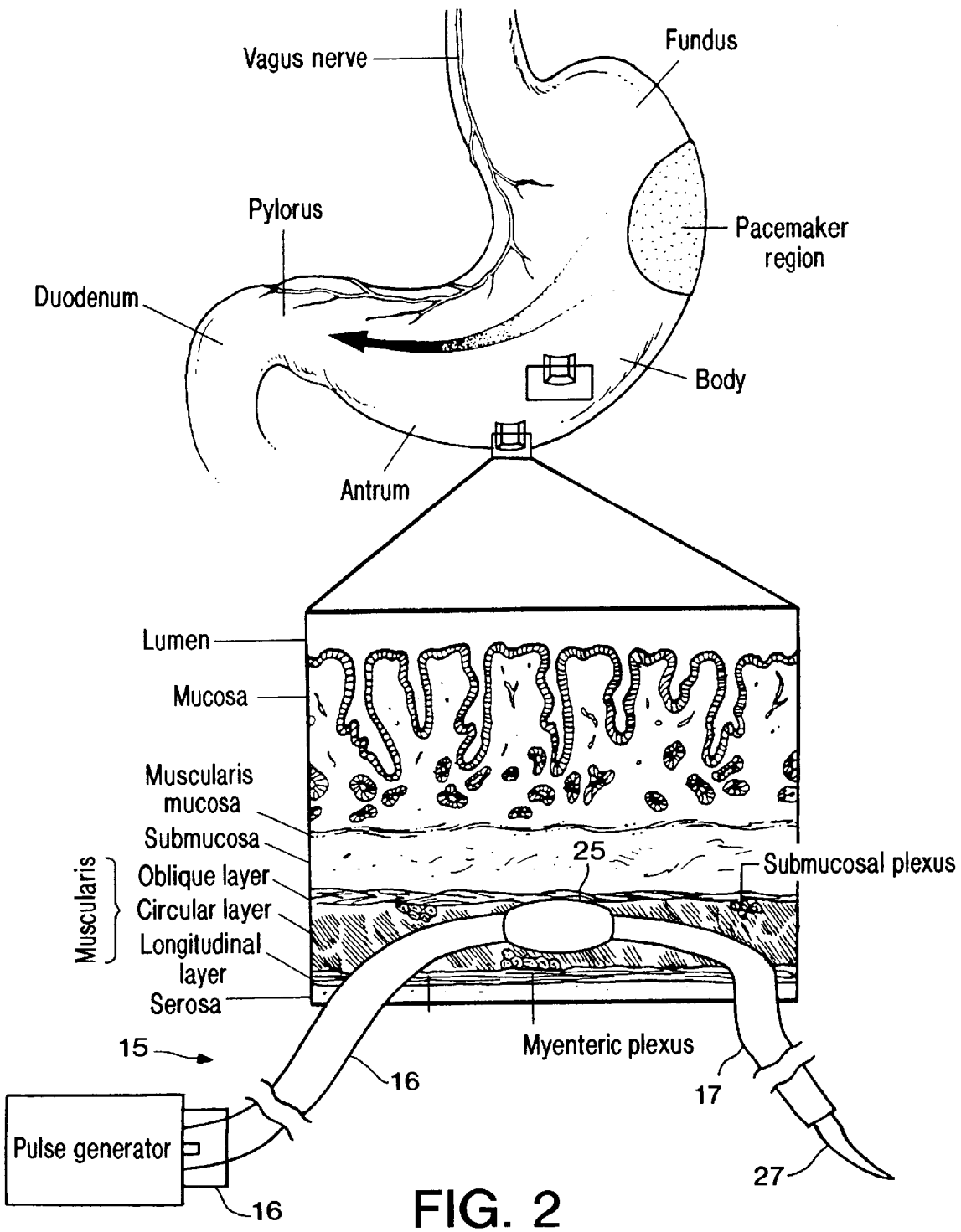
FIG. 2 depicts a detailed view of the stomach muscle showing the electrode of the lead implanted.

FIG. 2 details the preferred positioning of an electrode of a lead within the various layers of the stomach. As seen, the stomach 10 has essentially seven layers of tissue. In the preferred embodiment, the electrode of each lead is positioned into the layers of the stomach muscle as shown. That is, the electrode is positioned such that it intersects both the longitudinal and circular layers. This is believed important by the inventor because in such a manner the electrode is able to also intersect the enteric nervous system of the stomach and be in close contact with the cells of Cajal. This is believed important as research has shown that intramuscular electrodes may effectively stimulate the stomach with less than one one-thousandths of the energy required for serosal electrodes. Of course, other types of electrodes or lead systems may be used, including those which contact only any one of each of the layers of the stomach organ, such as only the mucosa or only the serosa. Moreover, although in the preferred embodiment a pair of unipolar leads are used for stimulation and a second pair of unipolar leads are used for stimulation, other configurations of leads may be used, such as bipolar, tripolar, quadrapolar, as well as any other configuration suitable such as a unipolar lead and can.

Figure 3:
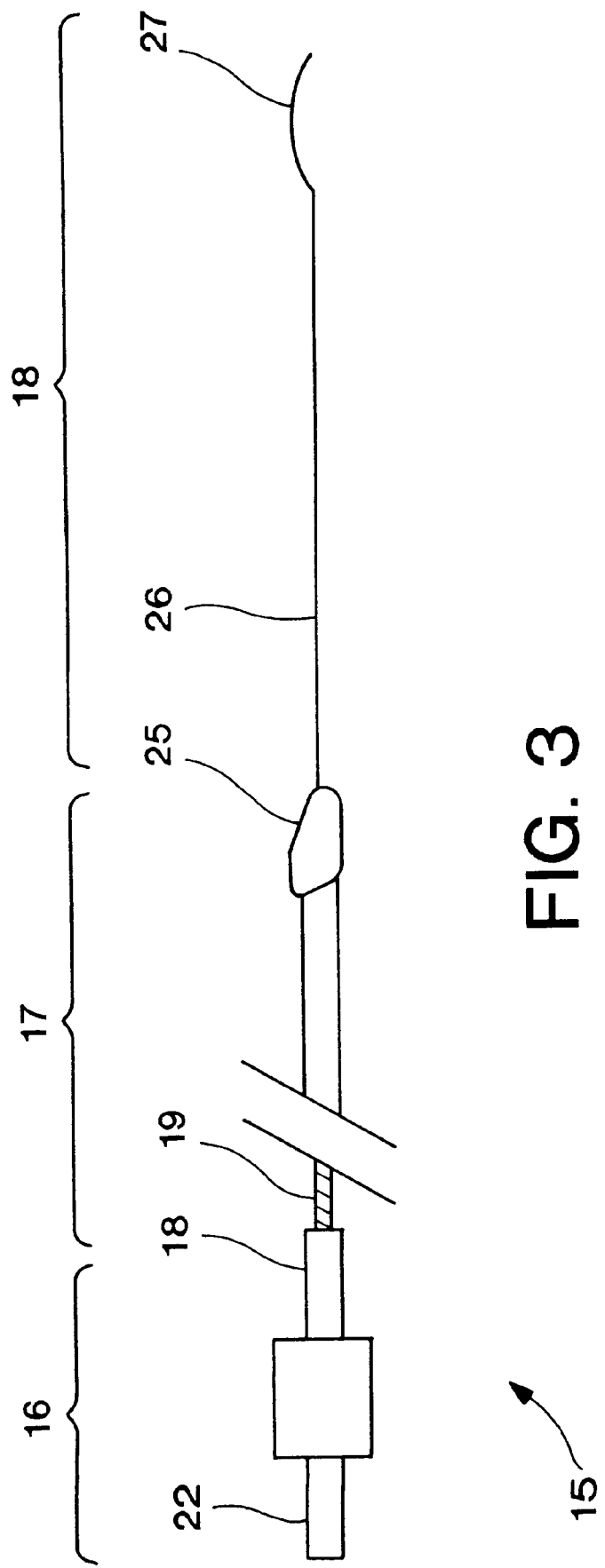
FIG. 3 depicts a plan view of a lead used with the apparatus.

FIG. 3 depicts a plan view of the preferred embodiment lead 15 used in the present invention. As seen, the lead 15 essentially has three sections, connector section 16, body section 17 and fixation section 18. Connector section 16 includes a connector pin 22 to electrically couple the lead 15 into the pulse generator. Any connector pin 22 as well known in the art may be used. Body section 17 includes an electrical conductor 19 surrounded by an electrical insulator 20. In the preferred embodiment electrical conductor 19 is a platinum iridium alloy and electrical insulator 18 is silicone. Of course, other biocompatible materials may also be used. As seen, at the distal end of the body section 17 is an electrode 25. In the preferred embodiment, electrode 25 is a polished platinum iridium alloy. Of course, other materials may likewise be used, such as a porous platinized structure. In addition, the electrode 25 could further feature various pharmaceutical agents, such as dexamethasone sodium phosphate or beclomethasone phosphate in order to minimize the inflammatory response of the tissue to the implanted lead 15. Other agents such as antibiotics may also be used. Located distal to the electrode 25 is the fixation section 18. As seen, fixation section 18 has essentially two piece parts, a suture 26 which is in turn coupled to a needle 27. Needle 27 is preferably curved. In an alternate embodiment suture may feature a fixation coil as is well known in the art to cooperate with the body tissue after implantation to maintain the lead 15 in the position implanted. Of course, other fixation mechanisms may be used, such as fixation discs, as is well known in the art.

Figure 4:
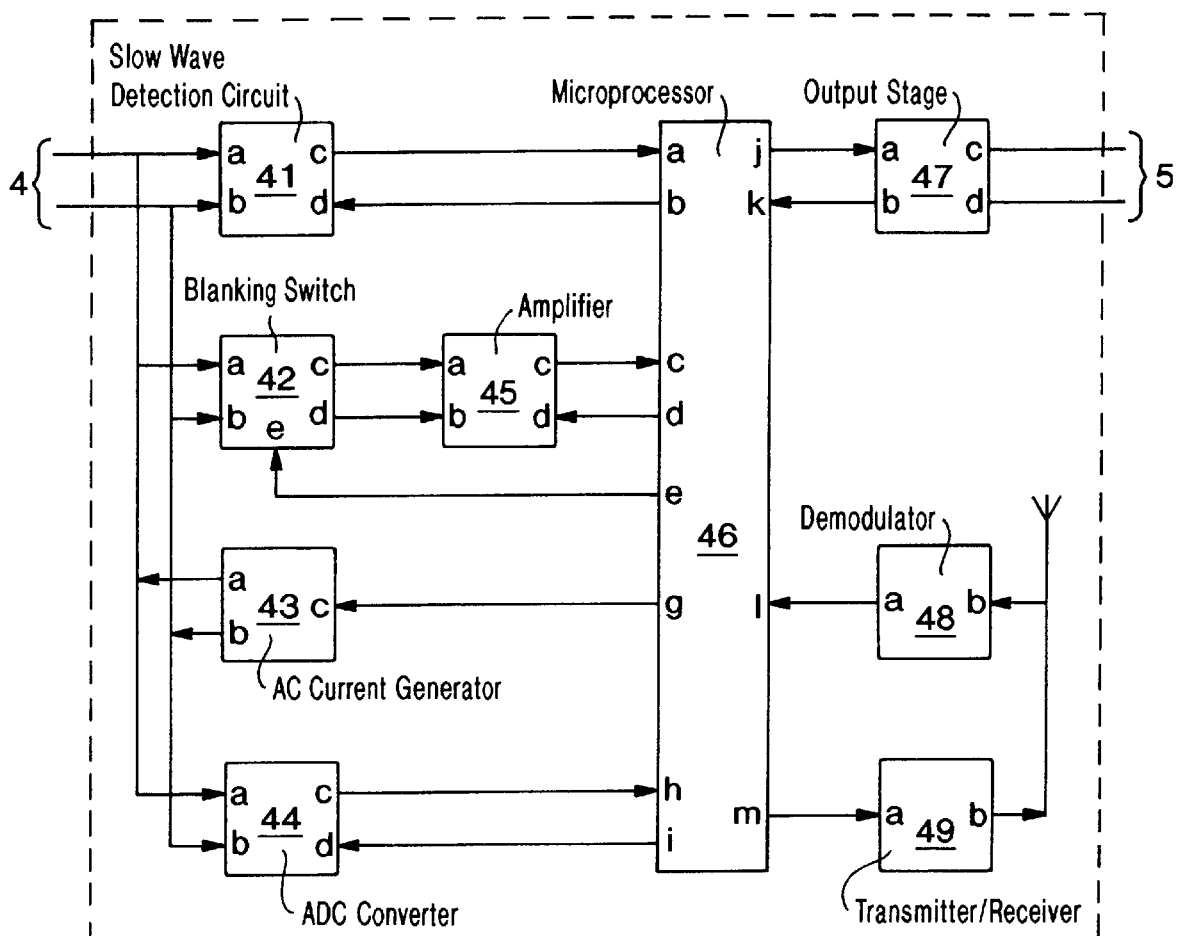
FIG. 4 is a functional block diagram of the pulse generator.

FIG. 4 depicts a functional block diagram of the gastrointestinal pulse generator according to the present invention. As seen, pulse generator 3 is enclosed by hermetic enclosure 40 to the electronics and battery while the device is implanted. Hermetic enclosure may consist of any suitable construction. Pulse generator 3 couples with two sets of leads 4, 5 which are, in turn, coupled to the stomach 10. The first set of leads 4 transmits stimulation pulses from pulse generator 3 to the stomach. The second set of leads 5 provide sensing of the gastroelectrical activity of the stomach 10 to the pulse generator 3. Although in the preferred embodiment the stimulating leads and sensing leads are separate leads, the present invention may also be employed using a combination of lead which both sense and stimulate.

As seen, the sensing leads 4 are coupled into a slow wave detection circuit 41. Slow wave detection circuit 41 includes a band pass amplifier, a slew rate converter and two threshold detectors. Essentially, such a slow wave detection circuit 41 is similar to those used in a cardiac pacemaker but with several important characteristics. First, the band pass amplifier has a much lower center frequency, preferably on the order of 0.3 HZ when used in the stomach. Of course, the present invention may be used in each of the various organs along the GI tract so that the center frequency may be varied accordingly. The slew rate converter operates in a manner well known in the art and generates a signal corresponding to the slew rate of the sensed electrogastrogram. The threshold detectors operates in a manner well known in the art and generate output signals when the sensed input signal is above a threshold level. One threshold detector corresponds to the peak to peak amplitude of the sensed electrogastrogram. The second threshold detector corresponds to the sensed slew rate.

Preferably, the slow wave detection circuit 41 must be able to detect input signals between approximately 30 microvolts and 10 millivolts which have a slew rate between 100 microvolts per/second up to 10 volts per/second with a typical value of 100 millivolts per second. Such a range may be achieved using multiple steps which are controlled by the microprocessor 46 via the input line 46b–41d. To detect the slow wave, both threshold detectors should be coupled using a logical AND configuration. Thus, a signal should then be sent via the output line 41c–46a to the microprocessor 46. The slew rate detector may also include an interference detector specially designed to detect continuous interference, especially at any of the various mains frequencies of power distribution (e.g. 16–400 Hz) so that false sensing is avoided. In an alternative embodiment a second sense amplifier may be provided having a bandpass in the range of expected power field variations in various frequencies of power distribution (e.g. 16–400 Hz). At every cycle the presence of interference is detected. The time interval between two detections is measured and if this time interval corresponds to any of the main frequencies of power distribution which is preprogrammed, then this detection is labeled as interference and the detection on the other amplifier will be simultaneously labeled also as interference detection and not as a valid slow wave.

The band pass amplifier in the detection circuit 41 should be blanked for a period after a sensed event has been received by the microprocessor 46 or just before and during a stimulation pulse is emitted by output stage discussed below. Blanking may be accomplished through either a blanking switch which disconnects the amplifier from the electrodes or through a program performed in the microprocessor. The microprocessor 46 should also ignore sensed output signals during a period after a sensed or paced event. This is similar to a blanking circuit where sensed events during a blanking period do not affect the timing of the pulse generator. In the preferred embodiment, the blanking period for slow wave detection is on the order of between 0.5 to 4.0 seconds.

Generally speaking, the blanking period decreases with increasing slow wave frequency. The blanking period algorithm is controlled by the microprocessor. The blanking period algorithm operates such that when the slow wave interval is shortened the blanking period is also shortened. This shortening may be performed in any manner, for example, in a linear fashion or in some other more complex monotonous fashion. After the blanking period, during a certain timing window, the microprocessor 46 is able to receive slow wave detection signals, which will not restart the pulse generator timing circuit, but will instead be interpreted as interference by the microprocessor 46. This timing window, interference detection timing window, may be up to seven seconds in duration after the sensed or paced event, preferably it is 100 milliseconds. To be precise, the combined blanking period and interference detection windows are shortened. Shortening may occur in any manner desired, i.e. in a linear fashion between a preset high or a preset low value or along a non-linear manner. The shortening of the combined blanking and interference detection interval will not occur once the combined blanking and interference detection window reaches a programmed value, such as 2.5 s. This combined blanking window may also be programmed to be turned off such that it does not change in response to sensed physiologic signals. In all circumstances, however, the interference detection window remains equal to at least 100 ms. For example, the rationale is that the typical main frequencies of power distribution are 50 Hz, 60 Hz, 400 Hz and 16.33 Hz. The lower harmonic for 1633 Hz is 8 Hz which corresponds to an interval of 125 ms. Of course the exact length of time for each period may be programmed by the physician. Moreover, each of the periods may be further made to be automatically adjusted based on the sensed electrical activity.

As seen in FIG. 4, blanking switch 42 couples sensing electrodes 4 to amplifier 45 to detect high frequency spike activity. The operation of blanking switch 42 causes the amplifier 45 to be connected to the sensing electrodes 4 once an intrinsic deflection or slow wave has been detected by slow wave detection circuit 41 or a stimulus has been emitted by output stage 47. Preferably, this occurs after a short delay. Blanking switch 42 is closed between 0.5 to 2 seconds after these events and opens roughly 5 to 7 seconds later or at approximately 30% of the intrinsic event interval. As seen, the switch is controlled via the line 46e–42e.

The detection circuit for the high frequency spike activity detector consists of a bandpass amplifier having the center frequency at approximately 300 Hz. As discussed above, however, the center frequency will vary for different organs. The amplifier is followed by two threshold detectors, the first detector detects peak to peak amplitude while the second detector detects slew rate. Both detectors are coupled using a logical AND configuration. The detector pulses are counted, and the interval between pulses is measured. If the interval corresponds to the intervals of the mains frequencies of power distribution or any of their harmonics, i.e. 20 ms or 10 ms, they are rejected. If the number of pulses exceeds a pre-programmed value, then a contraction is indicated. The counter is provided to store in the memory the time of occurrence of the contraction. The number of pulses corresponding to each contraction may be counted and tallied to determine the strength of the contractions. In the present embodiment 3–5 pulses correspond to a weak contraction; 6–8 pulses correspond to a moderate contraction; 9 or more pulses correspond to a strong contraction. Each of these values, of course, may be programmed and the exact number of pulses will vary due to the implementation.

Also coupled to the sensing electrodes 4 is an AC current generator 43. This AC current generator 43 is part of a plethysmorgraphy circuit. Overall, the plethysmography circuit is present to provide a means for sensing mechanical activity of the underlying tissue. That is, whereas the spike activity in the electrogastrogram may be used to sense contraction, the contraction may also be sensed using the plethysmography circuit. Plethsmography circuit is comprised from AC current generator 43, amplifier, modulator and ADC converter 44 as well as a portion of the microprocessor 46. The AC current generator 43 is switched on via signal from microprocessor 46 once a slow wave is detected or a pacing stimulus is emitted. It is switched off roughly 10 seconds after being switched on also from the same line or signal from the microprocessor 46. The AC current generator 43 amplitude and frequency are programmable via microprocessor 46. The frequency should be such it is not detected by amplifiers 41, 45, e.g., 1 kHz. If synchronous detection by amplifier 41 occurs at the end of the blanking period, then the amplitude and/or the frequency of the AC current generator 43 is adjusted by the microprocessor 46 to avoid subsequent detection of the generated AC current.

Turning now to the amplifier, the modulator and ADC converter 44, the AC voltage caused by the injection of AC current generator 43 is amplified and demodulated and converted in order to detect impedance changes caused by contractions of the underlying tissue. The ADC converter digitizes the amplitude of the demodulated signal. The digitized signal is transmitted via line 44c–46h to the microprocessor 46. The microprocessor 46 analyzes the signal pattern by comparing it with one or more templates to identify it as a contraction as well as to reject interference or signals generated by postural changes or vomiting. This template comparison is done synchronously to the detection of the slow wave. Line 46i–44d is used to control the amplifier and ADC from the microprocessor 46.

The microprocessor 46 handles all timings and data storage of the pulse generator and may be of any suitable design. In the preferred embodiment, a microprocessor 46 such as that used in the Thera I series of Medtronic pacemakers is used. The description of the microprocessor 46 function is described in the section below which details the operation of the algorithm used in the present invention.

Stimulation pulses are generated by the output stage 47. In the preferred embodiment, the output stage 47 generates pulse trains. It should be understood many types of pulse trains or stimulation pulses may be used including constant current or constant voltage outputs, or a mixture of both. The output pulses are transported to the gastrointestinal tissue via medical electrical leads 5 and thus to the stomach.

Turning again to the output stage 47, when an output pulse is to be delivered, its amplitude, pulse width and duration and frequencies are controlled via lines 46j–47a. If it is a burst of stimuli, the frequency and duration are controlled through the same line while a burst finished signal is sent to the microprocessor 46 via output line 47b–46k.

Programmability to the pulse generator 3 is achieved through receiver-demodulator 48 and transmitter 49. As seen, each of these devices is coupled to the microprocessor 46. The receiver-demodulator 48 and transmitter 49 are similar to those used in cardiac pacemakers.

The basic parameter settings such as sensitivity (peak voltage or slew rate), refractory, blanking, output pulse amplitude, pulse width, escape interval and ratio, escape interval to a stimulation interval, are stored in the memory of the microprocessor 46. Default values are also stored. These values can be read from memory and sent to a receiver via the transmitter.

Figure 5:
FIG. 5 is an electrogastrogram of the gastrointestinal system.

FIG. 5 shows an electrogastrogram of the stomach in a human. As seen, this intrinsic gastroelectric activity has two distinct components. The first component 501 is a low-frequency, rhythmic depolarization termed slow waves. Superimposed on the slow wave is a high frequency spike activity 502 which corresponds to mechanical contractions of the organ. In the human stomach slow waves are regular, omnipresent depolarizations at 3 cycles/min. (0.05 Hz) that commence high on the greater curvature of the stomach, in the region referred to as the pacemaker region, and propagate aborally, as depicted in FIG. 2.

The normal frequency range for the slow wave in the stomach is between 2.7–3.4 bpm. In clinical situations this value may vary anywhere between 1–15 bpm. High frequency slow wave activity (called tachygastria) does not permit contraction of the stomach readily and may even results in a gastroparesis. In the presence of excessively slow or even absent slow waves (called bradygastria) motility is reduced.

Slow waves and the corresponding spike activity may become irregular or uncoupled or both, thereby preventing the appearance or organization of regular, normally propagated contractions that constitute normal motility. Contractions cannot occur without gastric electrical response activity which is in turn regulated by the electrical control activity. Any disruption in this delicate sequential order may lead to delayed gastric emptying. An example of such an occurrence is shown in complex 505.

The spike activity occurs incidentally for a few of the slow waves while the patient is in a fasting or non-eating condition. This is termed Migratory Motor Complex phase 1. Immediately prior to a meal, typically 30 mins, MMC I changes into MMC II. During this phase the number of slow waves having spike activity increases. Once the meal or eating has begun and up to 120 mins after the meal each further slow wave also has a spike activity component. This condition is called MMC Ill.

As seen in this complex a slow wave 510 occurs which is not followed by any high frequency spike activity. The absence of such activity indicates there is no longer any peristaltic contraction which will occurs, i.e. gastric emptying is delayed.

Figure 6:
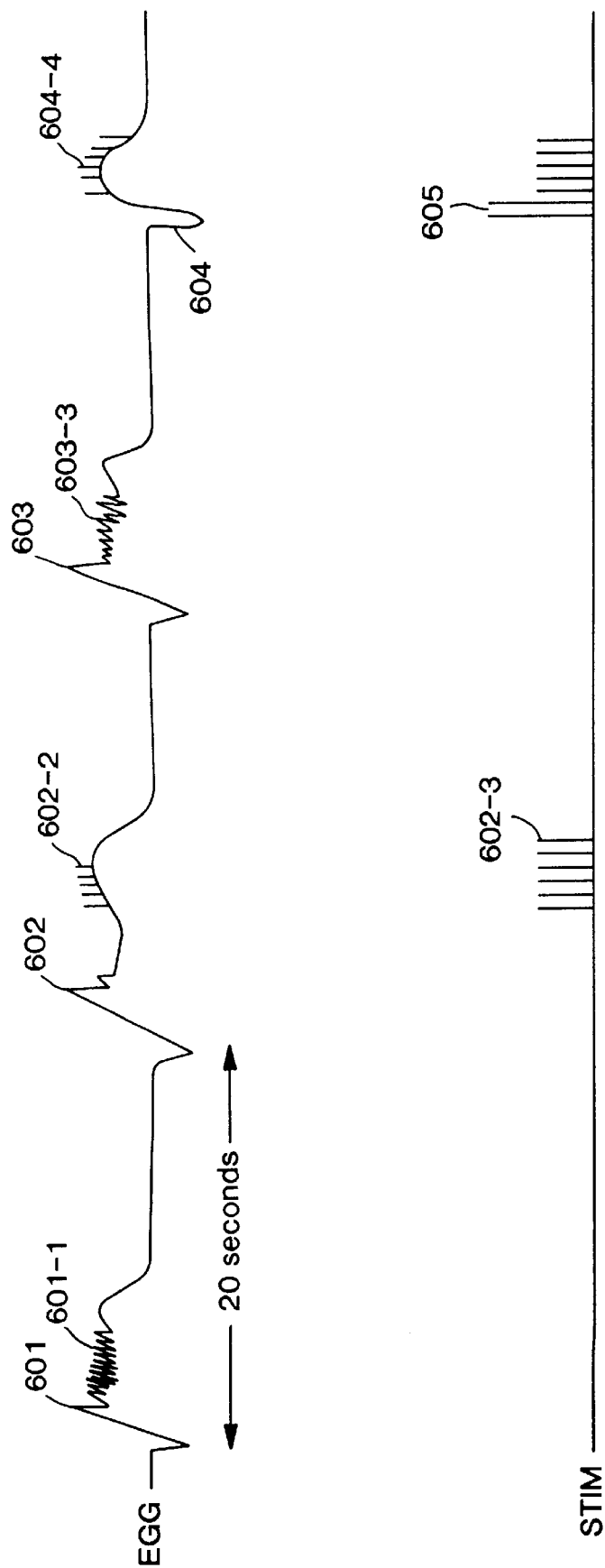
FIG. 6 is an electrogastrogram illustrating an arrhythmia and the response of the apparatus.

FIG. 6 depicts electrogastrogram tracings of a stomach illustrating the operation of the device to treat abnormal electrogastric activity. As seen, the stomach typically has periodic slow waves which occur at an intrinsic rate of 3 beats per minute or approximately 20 seconds apart. These intrinsic slow waves typically occur at a relatively fixed rate. Here, these fixed, periodic slow waves are shown as waves 601, 602 and, 603. In a normal electrogastrogram taken during a meal, each slow wave features a high frequency spike activity, such 601-1 and 603-3. This high frequency spike activity is a sign of contraction by the muscle, indicating normal motility.

As seen at slow wave 602, however, no high frequency spike activity is present. This indicates a lack of peristaltic waves in the stomach and thus diminished motility. As discussed above, the present invention detects such diminished motility and delivers electrical stimulation. In particular, the pulse generator features two sensor. The first sensor senses slow waves, like 601, 602 and 603. The second sensor senses spike activity, like 601-1 and 603-3. The pulse generator further delivers stimulation pulse trains to the gastrointestinal tract at a period of time after slow waves have been sensed by the first sensor. If, however, the second sensor senses intrinsic spike activity between the frequency of 100–5000 Hz, then the delivery of stimulation pulse trains to the gastrointestinal tract is inhibited. In such a manner the present invention provides electrical stimulation to the gastrointestinal tract at all times except when normal gastric activity is detected. At 604 the slow wave rate interval has timed out and a pulse train consisting of a slow wave escape stimulation is delivered at 605. As seen in this illustration 605 is a pulse train with two components, a low frequency high amplitude front followed by a lower amplitude higher frequency end.

Figure 7:
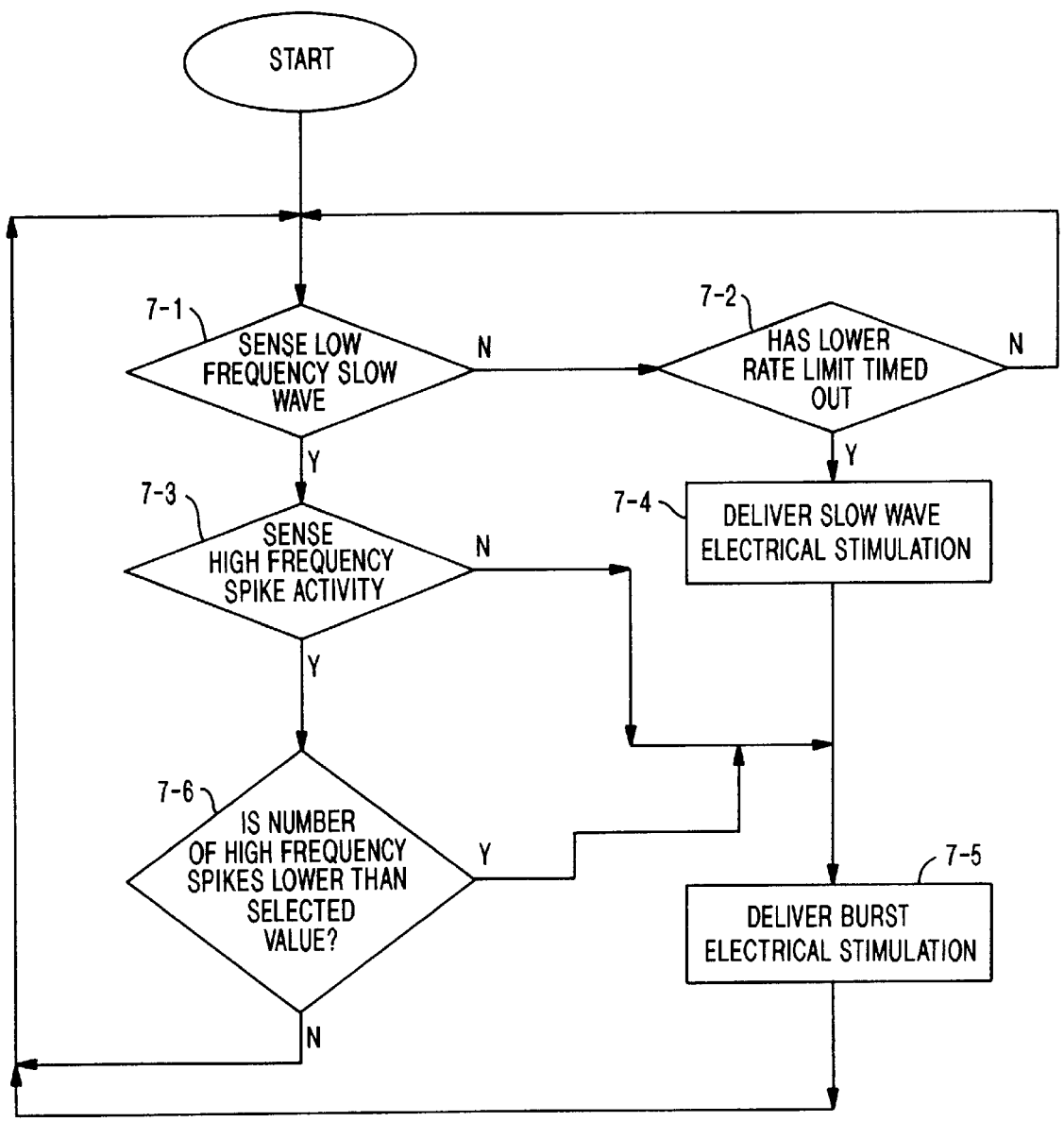
FIG. 7 is a flowchart depicting the operation of the system.

FIG. 7 is a flowchart of the present invention. FIG. 7 is a flow chart of the present invention. As seen, in operation, the invention generally requires sensing of the two distinct waves or electrical signals in the EGG, low frequency slow waves and high frequency spike activity. As discussed above, slow waves are sensed in the frequency range of approximately 0.005–5 Hz while spike activity is sensed in the range of approximately 100–5000 Hz. At step 7-1 slow waves are sensed. If no slow waves are sensed then the device proceeds to step 7-2 with the lower rate timer operating. As seen, if the lower rate limit timer is not timed out, then the device resets and continues looping between step 7-1 and step 7-2. If the lower rate timers is timed out then the device proceeds to step 7-4 and delivers slow wave electrical stimulation. As discussed above, slow wave electrical stimulation is delivered to normalize the slow waves in the stomach which have been found to be an effective treatment for the symptoms of gastroparesis, e.g. nausea or vomiting. Slow wave electrical stimulation may comprise either a single pulse or a series of pulses delivered at a frequency of 10–100 Hz having an amplitude of 3 V and a pulse width of 330 ms. If a low frequency slow wave is sensed at step 7-1, however, then the device proceeds to determine whether any spike activity is sensed. Once the slow wave electrical stimulation is delivered the device proceeds to step 7-5 and delivers burst electrical stimulation. The burst electrical stimulation is delivered at step 7-5 in order to elicit or cause a contraction of the stomach. If spike activity is sensed, then the device proceeds to step 7-6, and determines whether the number of spikes is lower than a selected value. If the number of spikes is lower than the selected value, then an adequate contraction of the stomach is deemed not to have occurred and the device proceeds to step 7-5 where it delivers burst electrical stimulation to thereby cause a contraction of the stomach. If, however, sufficient number of spikes are sensed in step 7-6, then the device is reset and proceeds again through the loop beginning at step 7-1. Through this algorithm it is thus seen that the device continuously monitors first, whether slow waves occur in the stomach and, if they are not occurring, delivers slow wave electrical stimulation followed by burst electrical stimulation. If, however, slow waves are sensed then the device determines whether or not spike activity is following. If an insufficient amount of spike activity is following then burst electrical stimulation is delivered to thereby cause a contraction. If sufficient high frequency spike activity is occurring then the device resets itself arid again senses for slow waves. For example, as discussed above, the device may be programmed to detect spike activity and count the number of spikes sensed associated to each corresponding slow wave. This number of spikes corresponding to each slow wave and thus each contraction may be counted and tallied to determine or assess the strength of the contractions. In the preferred embodiment 3–5 spikes correspond to a weak contraction; 6–8 spikes correspond to a moderate contraction and 9 or more spikes correspond to a strong contraction. Each of these values, of course, may be programmed and the exact number of spikes necessary to achieve the corresponding characterization of the contraction will vary due to the organ in which the device is used.

Figure 8A:
FIG. 8a–8e depict various pulse trains which may be emitted by the present system.

FIG. 8a depicts a pulse train used in the present invention. As seen, the preferred pulse train 300 is emitted at a frequency of 30 Hz and has a duration of approximately 4 seconds, each pulse lasting 330 microseconds with an amplitude of 0.5 to 10 Volts or a current of between approximately 0.1 milliamps to 30 milliamps. In an alternative embodiment all of the stimulation may be programmed as well as the waveforms used and their phase.

Figure 8B:
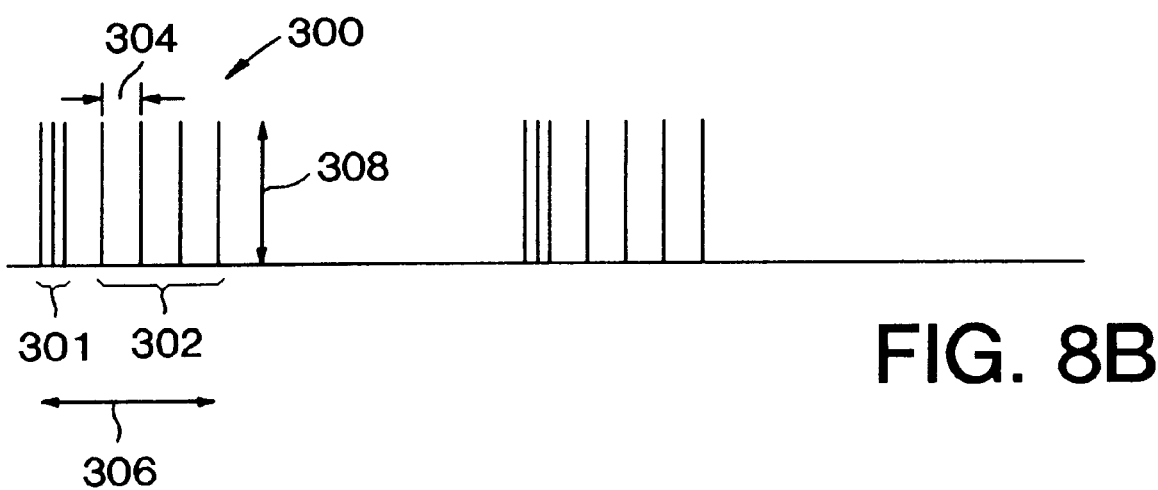

FIG. 8b depicts an alternate pulse train which may be used with the present system. Muscle stimulation burst 300 has essentially two section, first section 301 and second section 302. As seen, first section 301 has a smaller interpulse interval 304 within the burst, i.e. a higher frequency. In comparison second section 302 has a relatively larger interpulse interval 304 within the burst, i.e. a relatively smaller frequency. In the preferred embodiment interpulse interval 304 and number of pulses in the first section may be selected by the physician. The pulse waveform and amplitude 308 are the same for the remainder of the burst.

Figure 8C:
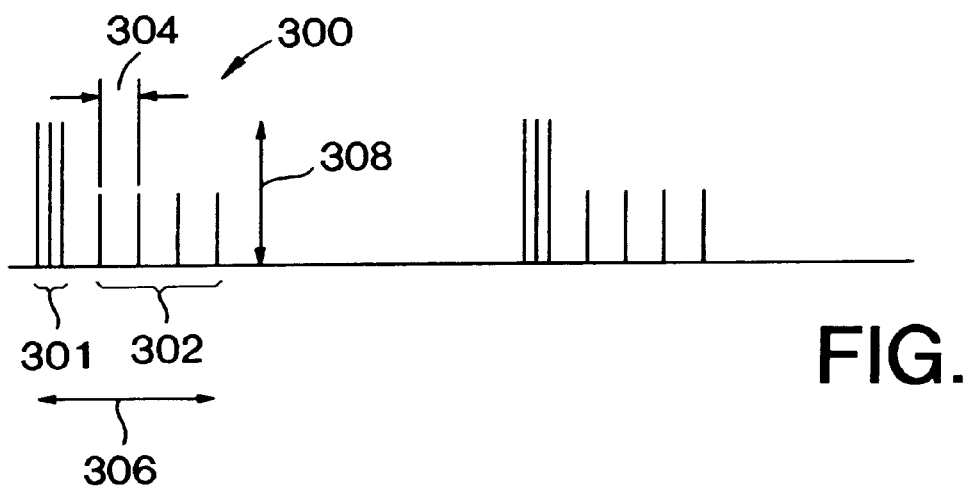

FIG. 8c depicts an alternate embodiment of a pulse train which may be used with the present system. As seen all parameters of the muscle stimulation burst 300 are the same as that described above with respect to FIG. 8a but for the amplitude of second section 302.

Figure 8D:
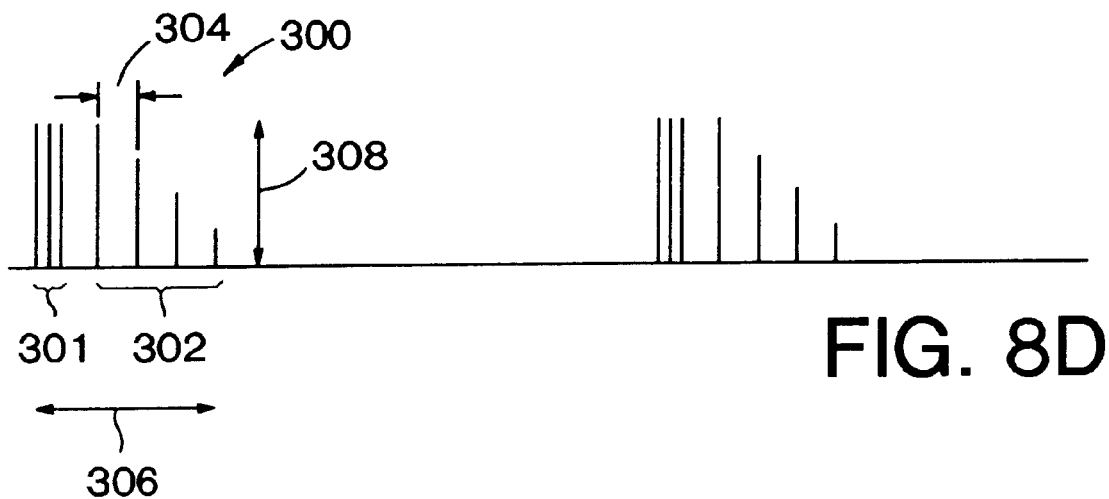

FIG. 8d depicts an alternate embodiment of a pulse train which may be used with the present system. As seen all parameters of the muscle stimulation burst 300 are the same as that described above with respect to FIG. 7 but for the amplitude of second section 302. In particular amplitude of each burst within second section 302 decreases.

Figure 8E:
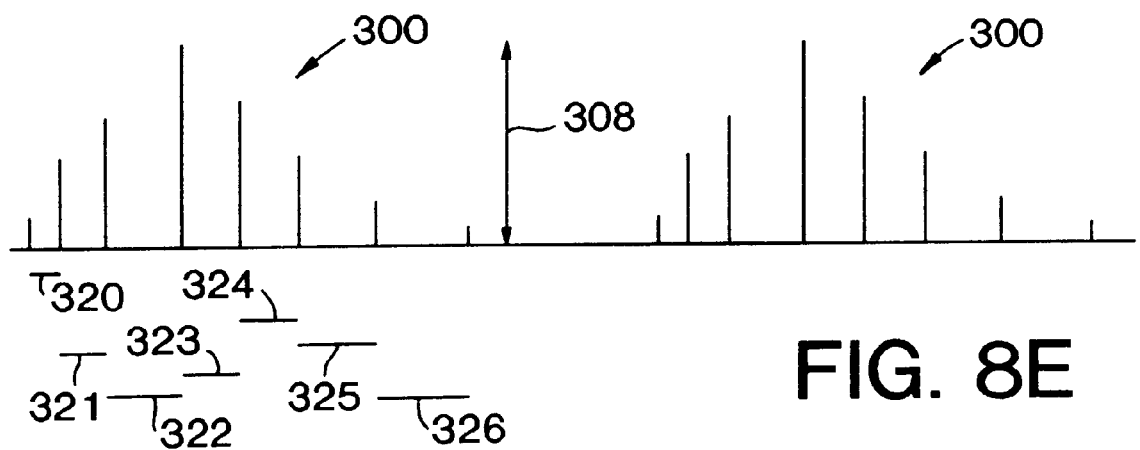

FIG. 8e depicts an alternate embodiment of a pulse train which may be used with the present system. As seen burst 300 consists of a number of pulses 309. The amplitude of each pulse 309 differs from the amplitude of each preceding and following pulse. In addition, the interpulse interval between each pulse 309 is different. None of 320, 321, 322, 323, 324, 325 or 326 are equal to another. Each of the various parameters, such as amplitude 308 and the rate of change of amplitude 308, synchronization delay 305 and interpulse intervals 320, 321, 322, 323, 324, 325 and 326 are programmed on a patient by patient basis so as to attain the most efficient stimulation while minimizing energy expenditure. Of course other unique waveforms of pulse trains may also be used, such as biphasic or poly phasic for example. In addition each of the above identified various parameters, including frequency, amplitude, rate of change of amplitude, rate of change of interpulse interval, etc. may be programmed on a patient by patient basis so as to attain the most efficient stimulation while minimizing energy expenditure.

From a system component viewpoint the system operates as follows. Upon the detection of a sensed slow wave or a principal stimulated event, the escape timer is reset and starts counting. A stimulation pulse or pulse train will be emitted at the end of the timing out of the escape timer. If however, a slow wave is detected after the end of the refractory period and before the escape interval times out, then the stimulation is inhibited and the counters are reset. This occurs in the inhibited mode, similar to WI cardiac pacing. If, however, ratio escape interval to a stimulation interval is programmed, e.g., a value of 5 and the escape interval is 20 seconds, then stimulation pulses would be emitted every 4 seconds but stimulation during the refractory period will not reset the escape timer.

If a contraction occurs, spike activity is seen in the electrogastrogram. To avoid saturation of the slow wave detection circuit 41 of spike activity, the amplifier is connected via a switch to the connecting electrodes. This switch connects the amplifier to the sensing electrodes once an intrinsic deflection has been detected or a stimulus has been emitted. This could occur after a short delay. The switch is closed roughly 0.5–2 seconds after the above events, and closes roughly 5–7 seconds later or at 30% of the intrinsic interval. The switch is controlled via the line 46e–42e from the microprocessor 46. Each confirmation of a detected spike and the interval between two detections is stored in the memory of the microprocessor 46. When the blanking switch is opened, the microprocessor 46 calculates the number of spikes sensed. If the number of spikes sensed is above a set level, for example, 7, and if the interval between the spikes does not correspond to the interval of the main frequency or multiples from it, then the microprocessor 46 confirms a mechanical contraction has been sensed. This event, with its time of occurrence, is stored in memory.

Another method which may be used to detect mechanical contractions of the underlying tissue is plethysmorgraphy. Plethysmorgraphy may be used to validate the high frequency spike activity detection or programmed on if the electrodes are at locations where no high frequency spike activity may be sensed. The operation of the plethysmorgraphy circuit is as follows. The current generator injects an AC current between 100 microamps and 10 milliamps at a frequency of 1 kilohertz to 20 kilohertz between the two sensing electrodes or a sensing electrode and the implantable pulse generator can, as is well known in the art. The current generator is switched on a few seconds (1–3 seconds) after the detection of a slow wave or after the emission of a principle stimulus. The current generator is then switched off roughly 7 to 10 seconds later after the detected event. The amplifier could have a front end switch to avoid saturation by stimulation or the slow wave. The operation of the switch and timing is identical to that discussed above with regards to the blanking switch, but the total interval the switch is left open is longer, 7–10 seconds, due to the electrical mechanical delay of the underlying tissue. In case of sampling the impedance wave form, it could be made to be either synchronous or asynchronous to the AC current source.

The sequential digitized signals sensed using the sensing electrodes are compared with templates collected and stored in the microprocessor 46. In the preferred embodiment, the templates are collected during the migrating motor complex phase at which no spike activity is detected. Such a phase is created during a learning period of the pulse generator so that the templates may be collected and stored. The migrating motor complex phase includes postural changes, coughing and perhaps even hurling. The learning period of the pulse generator should also include periods when the patient is prandal and when spike activity is detected. A template corresponding or useful to identifying vomiting may be collected as follows. If the amplitude of the measured signal exceeds the highest value during the migrating motor complex phase of the learning period of the pulse generator and no vomiting occurred during that time, then the sensed signal should be concluded as being or corresponding to vomiting.

Figure 9:
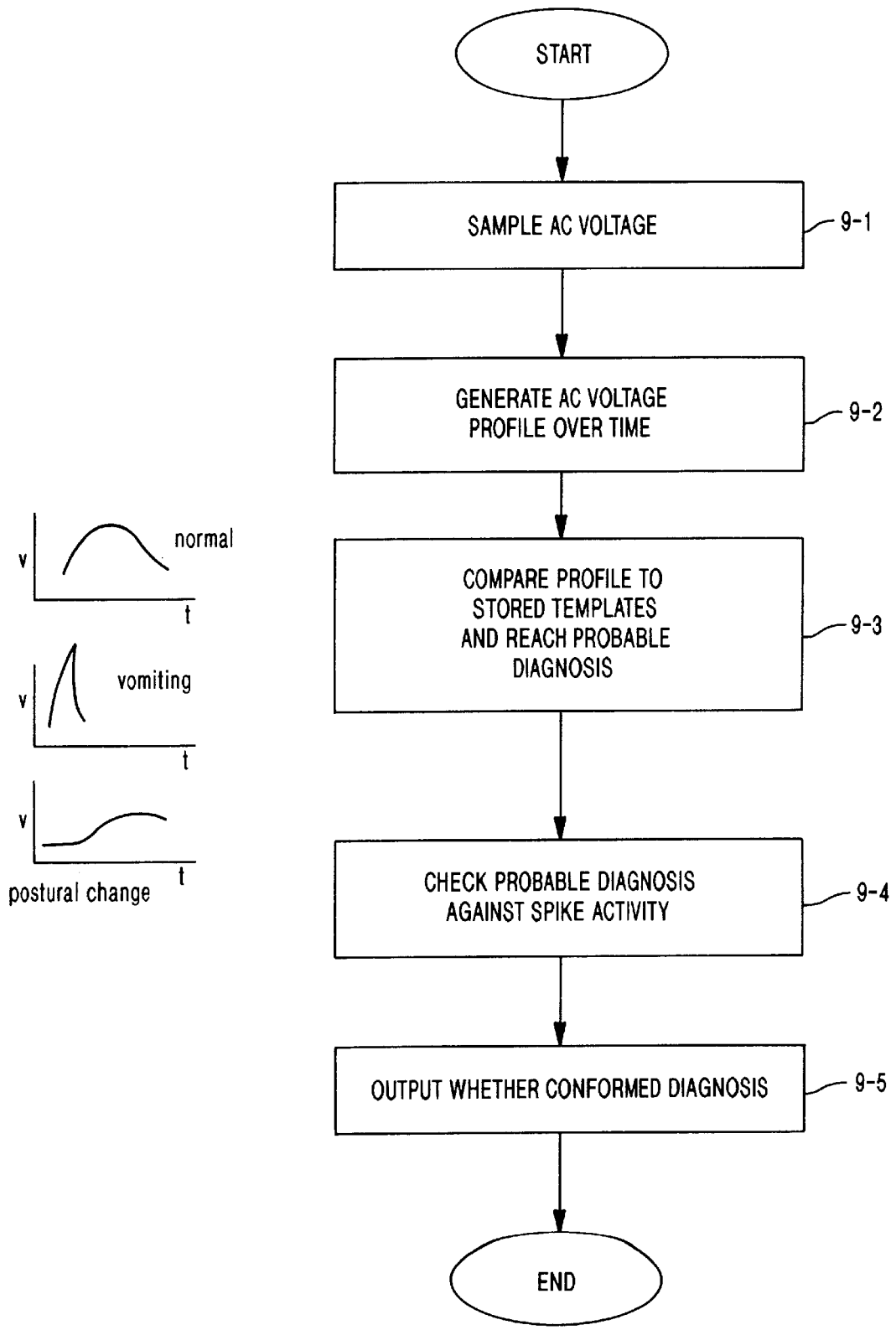
FIG. 9 depicts the steps used in the present invention to determine contraction or vomiting or other changes in the stomach using plethsmography.

FIG. 9 depicts the specific steps used in the present invention to determine contraction or vomiting or other changes in the stomach using plethsmography. At 9-1 the voltage resulting from the injection of AC current is sampled. At 9-2 the AC voltage profile is generated over time. At 9-3 the generated AC voltage profile is compared to stored templates to reach a probable diagnosis. Examples of such stored templates are further shown, e.g. the change in AC voltage due to a normal contraction, vomiting or a postural change. At 9-4 the probable diagnosis is compared against whether any spike activity is detected. At 9-5 an output of whether the diagnosis is confirmed is provided.

At each stimulus emitted or every preset numbers of stimuli, the electrode tissue impedance is measured. Such a scheme is well known in the art as seen in the Medtronic Itrel Ill Nerve Stimulator. If the electrode tissue impedance increases significantly between two measurements or if the electrode tissue impedance exceeds a preset level, then one may conclude the stimulation will be ineffective and an electrode may be dislodged. From that time forward the stimulator is switched to an off position so that no output signals are sent.

Figure 10:
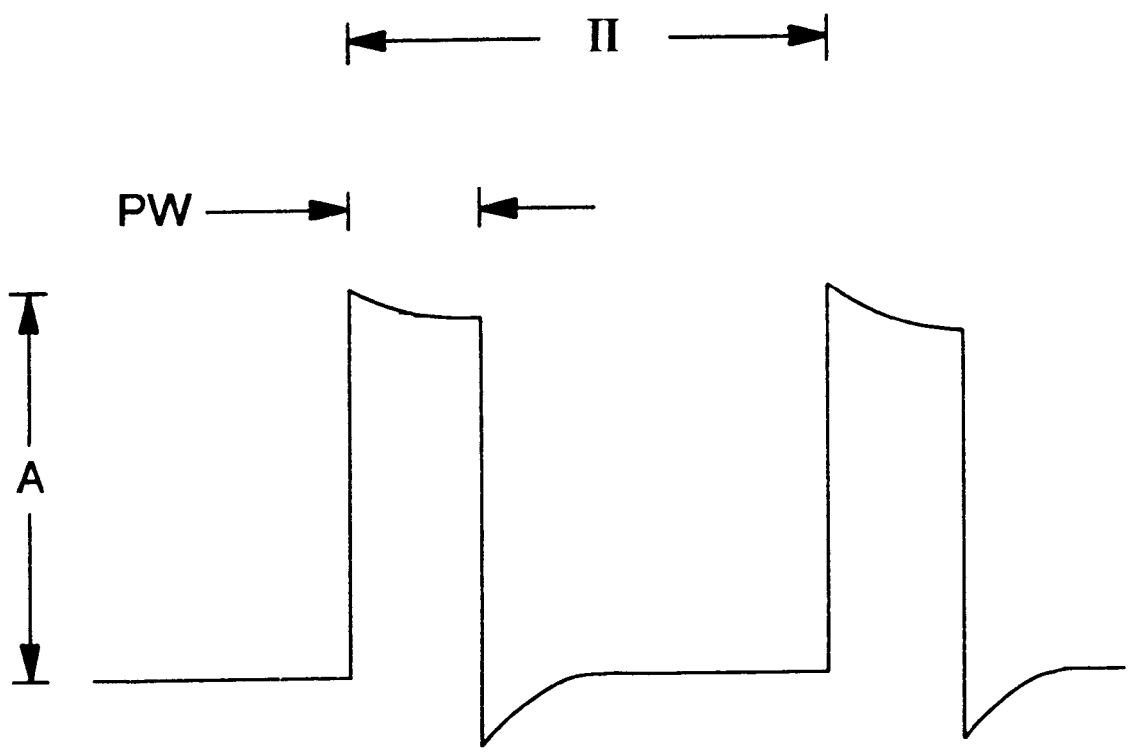
FIG. 10 depicts the electrical stimulation delivered in the normal mode of the device.

FIG. 10 depicts the electrical stimulation delivered in the normal mode of the device. Electrical stimulation preferably consists of a pulse train delivered at a rate of between 7–27 bpm with 12 bpm preferred. As seen, the pulse train preferred consists of two pulses, the pulse having an amplitude A, a pulsewidth PW and an pulse interval II. II may be anywhere between 6–600 ms in length with 60 ms preferred, A is between 1–50 milliamps with 5 milliamps preferred and pulsewidth is between 3–1000 microsecs with 330 microsecs preferred. Moreover, although the pulse train consisting of two pulses is preferred, any number of pulses between 1–100 may be used. As discussed above, the exact parameters selected depend not only on the organ to be stimulated but also upon the patient's physiology as well as on the preference of the physician attending.

While the present invention has been described in detail with particular reference to a preferred embodiment, it will be understood variations and modifications can be effected within the scope of the following claims. Such modifications may include substituting elements or components which perform substantially the same function in substantially the same way to achieve substantially the same result for those described herein.

What is claimed is:

1. An apparatus for providing electrical stimulation to the gastrointestinal tract comprising:

means for electrically coupling to the gastrointestinal tract;

a first sensor for sensing intrinsic gastrointestinal electrical activity between the frequency of 100–300 Hz, the sensor coupled to the means for electrically coupling to the gastrointestinal tract, the sensor emitting an intrinsic gastrointestinal electrical activity signal upon the sensing of intrinsic gastrointestinal electrical activity;

a pulse generator coupled to the means for electrically coupling to the gastrointestinal tract and the first sensor, the pulse generator emitting asynchronous stimulation pulse trains at a first rate, the pulse generator inhibiting the emission of asynchronous stimulation pulse trains at a first rate upon the emission of the intrinsic gastrointestinal electrical activity signal by the first sensor.

2. The apparatus according to claim 1 wherein the stimulation pulse trains comprise a series of pulse trains emitted at a frequency of 30 Hz and a duration of approximately 4 seconds, each pulse lasting 330 microseconds with an amplitude of between approximately 0.5 to 10 Volts or a current of between approximately 0.1 milliamps to 30 milliamps.

3. The apparatus according to claim 1 wherein the pulse train having a first section and a second section, the first section having a first frequency, the second section having a second frequency.

4. The apparatus of claim 3 wherein the first frequency is greater than the second frequency.

5. The apparatus of claim 3 wherein the first frequency is less than the second frequency.

6. The apparatus of claim 3 wherein the first section has a first amplitude, the second section has a second amplitude.

7. The apparatus of claim 3 wherein the first amplitude is less than the second amplitude.

8. An apparatus for providing electrical stimulation to the gastrointestinal tract comprising:

means for electrically coupling to the gastrointestinal tract;

a first sensor for sensing low frequency gastrointestinal electrical activity between the frequency of 0.017–0.25 Hz, the sensor coupled to the means for electrically coupling to the gastrointestinal tract, the sensor emitting a low frequency gastrointestinal electrical activity signal upon the sensing of low frequency gastrointestinal electrical activity;

a second sensor for sensing intrinsic gastrointestinal electrical activity between the frequency of 100–300 Hz, the sensor coupled to the means for electrically coupling to the gastrointestinal tract and the first sensor, the second sensor emitting an intrinsic gastrointestinal electrical activity signal upon the sensing of intrinsic gastrointestinal electrical activity between the frequency of 100–300 Hz within a pre-set period after the emission of a low frequency gastrointestinal electrical activity signal by the first sensor;

a pulse generator coupled to the means for electrically coupling to the gastrointestinal tract, the first sensor and the second sensor, the pulse generator emitting asynchronous stimulation pulse trains at a first rate, the pulse generator inhibiting the emission of asynchronous stimulation pulse trains at a first rate upon the emission of the intrinsic gastrointestinal electrical activity signal by the second sensor.

9. A method of electrically stimulating an comprising the steps of:

sensing low frequency slow waves in the gastrointestinal tract;

determining whether the sensed low frequency slow waves a exceeds predetermined slow wave amount;

delivering slow wave electrical stimulation if the sensed low frequency slow waves do not exceed the predetermined slow wave amount and delivering burst electrical stimulation;

sensing high frequency spike activity in the gastrointestinal tract;

determining whether the sensed high frequency spike activity exceeds a predetermined fast wave amount; and delivering burst electrical stimulation if the sensed high frequency spike activity is lower than the predetermined fast wave amount.

10. The method of electrically stimulating an organ of claim 9 wherein the step of sensing low frequency slow waves comprises sensing gastrointestinal electrical activity between the frequency of approximately 0.017–0.25 Hz.

11. The method of electrically stimulating an organ of claim 9 wherein the step of sensing high frequency spike activity comprises sensing gastrointestinal electrical activity between the frequency of approximately 100–5000 Hz.

12. The method of electrically stimulating an organ of claim 9 wherein the step of sensing high frequency spike activity comprises sensing gastrointestinal electrical activity between the frequency of approximately 100–5000 Hz for only a preset period of time after the step of sensing low frequency slow waves.

13. The method of electrically stimulating an organ of claim 9 wherein the step of delivering slow wave electrical stimulation comprises a series of pulse trains emitted at a frequency of 30 Hz and a duration of approximately 4 seconds, each pulse lasting 330 microseconds with an amplitude of between approximately 0.5 to 10 Volts or a current of between approximately 0.1 milliamps to 30 milliamps.

14. The method of electrically stimulating an organ of claim 15 wherein the step of delivering burst electrical stimulation comprises delivering a series of pulse trains emitted at a frequency of 30 Hz and a duration of approximately 4 seconds, each pulse lasting 330 microseconds with an amplitude of between approximately 0.5 to 10 Volts or a current of between approximately 0.1 milliamps to 30 milliamps.

15. A method of electrically stimulating an organ comprising the steps of:

determining the fullness of an organ within the GI tract;

sensing the absence of muscular contractions in the organ; and delivering an electrical muscular contraction stimulation to the organ to thereby cause a contraction to occur in the organ.

16. The method of electrically stimulating an organ of claim 15 wherein the step of sensing the absence of muscular contractions in the organ comprises:

sensing low frequency slow waves; and sensing gastrointestinal electrical activity between the frequency of approximately 100–5000 Hz for only a preset period of time after the step of sensing low frequency slow waves.

17. An apparatus for providing electrical stimulation to the gastrointestinal tract comprising:

a pulse generator, the pulse generator generating electrical stimulation pulse trains at a pre set frequency, means for sensing low frequency slow waves in the gastrointestinal tract; and means for sensing high frequency spike activity in the gastrointestinal tract for a first pre set period of time after the sensing of low frequency slow waves, the means for sensing high frequency spike activity coupled to the pulse generator and inhibiting the generation of the electrical stimulation pulse trains for a second pre set period of time when the sensed high frequency spike activity exceeds a programmed high frequency spike activity value.

18. The apparatus of claim 17 wherein the means for sensing low frequency slow waves comprises means for sensing gastrointestinal electrical activity between the frequency of approximately 0.017–0.25 Hz.

19. The apparatus of claim 17 wherein the means for sensing high frequency spike activity for a first pre set period of time after the sensing of low frequency slow waves comprises means for sensing gastrointestinal electrical activity between the frequency of approximately 100–5000 Hz.

* * * * *

UNITED STATES PATENT AND TRADEMARK OFFICE
CERTIFICATE OF CORRECTION

PATENT NO.     : 5,995,872
DATED          : November 30, 1999
INVENTOR(S)    : Bourgeois It is certified that error appears in the above-identified patent and that said Letters Patent is hereby corrected as shown below:

Column 12,
Line 62, change "stimulating an comprising" to -- stimulating and comprising --.

Signed and Sealed this

Twenty-fifth Day of March, 2003

JAMES E. ROGAN
*Director of the United States Patent and Trademark Office*